United States Patent [19]

King et al.

[11] Patent Number: 5,486,364
[45] Date of Patent: Jan. 23, 1996

[54] READILY AVAILABLE KONJAC GLUCOMANNAN AS A SUSTAINED RELEASE EXCIPIENT

[75] Inventors: Victor L. King, Ewing, N.J.; Thomas A. Wheatley, Richboro, Pa.; David F. Erkoboni, Lawrenceville, N.J.

[73] Assignee: FMC Corporation, Philadelphia, Pa.

[21] Appl. No.: 290,457

[22] Filed: Aug. 15, 1994

Related U.S. Application Data

[63] Continuation of Ser. No. 998,335, Dec. 30, 1992, abandoned.

[51] Int. Cl.$^6$ ............... A61K 9/22; A61K 9/10; A61K 47/36
[52] U.S. Cl. ............ 424/488; 424/465; 424/468; 424/409; 514/960; 514/961
[58] Field of Search ............... 424/488, 409, 424/464, 465, 499, 195.1, 78.17, 78.38; 514/960, 961, 777, 54; 426/72, 73, 658; 536/114, 127, 128

[56] References Cited

U.S. PATENT DOCUMENTS

| | | | |
|---|---|---|---|
| 3,928,322 | 12/1975 | Sugiyama et al. | 424/195.1 |
| 4,746,528 | 5/1988 | Prest et al. | 426/573 |
| 4,894,250 | 1/1990 | Musson et al. | 426/573 |
| 4,994,276 | 2/1991 | Baichwal et al. | 424/440 |
| 5,096,714 | 3/1992 | Kuhrts | 424/466 |

FOREIGN PATENT DOCUMENTS

| | | | |
|---|---|---|---|
| 2531339 | 2/1984 | Belgium . | |
| 0253541 | 1/1988 | European Pat. Off. | A61K 9/22 |
| 2523446 | 9/1983 | France | A61K 47/00 |
| 901111 | 3/1985 | France | A61K 47/00 |
| 57185216 | 11/1988 | Japan . | |
| 443819 | 8/1992 | Japan . | |

OTHER PUBLICATIONS

"Formulating For Controlled Release with Methocel Cellulose Ethers", Bulletin of Dow Chemical Company (1987).
Chronotherapeutic Release from Direct Compression Tablets Using Heterodisperse Polysaccharides, Stainforth, et al. extended Abstract of Paper presented at AAPS Meeting, Washington, D.C. pp. 18–21, 1991.
Preparatin and Dissolution Characteristics of Pullulan Tablets Ohta, et al., Kobunshi Ronbunshu, vol. 42, No. 11, pp. 817–823 (Nov. 1985).
Konjac Flour and Properties and Applications, Richard J. Tye, Food Technology (Mar. 1991).

*Primary Examiner*—Edward J. Webman
*Attorney, Agent, or Firm*—Anthony L. Cupoli; Mark A. Greenfield; Robert L. Andersen

[57] ABSTRACT

A solid dosage form, such as a pharmaceutical tablet, containing a rapidly hydratable konjac glucomannan sustained release excipient such as clarified konjac, cryogenically ground konjac and plasticized konjac. The method of making the tablets by compressing excipient and pharmaceutically active ingredient as dry powders.

24 Claims, No Drawings

READILY AVAILABLE KONJAC GLUCOMANNAN AS A SUSTAINED RELEASE EXCIPIENT

This application is a continuation of application Ser. No. 07/998,335, filed 12/30/92, abandoned.

BACKGROUND OF THE INVENTION

1. Field of the Invention

This invention relates to solid dosage forms and sustained release excipient materials, particularly those including konjac.

2. Statement of Related Art

Sustained release excipients are compositions that enable drug release over a period of time on a predetermineable basis. They are incorporated into formulations containing active ingredients to provide a sustained release of those active ingredients from the formulation. Typically, sustained release excipients are incorporated in a solid dosage form such as a pharmaceutical tablet which is designed to release the active ingredient over an extended time period.

Konjac (*Amorphophallus konjac*) is a plant, the tuber of which is the source of a well-known foodstuff in China and Japan, namely konjac flour. This flour, which contains a variety of insoluble materials described below as well as a major amount of desirable water-soluble substances, comprises a highly viscous sol of glucomannan and soluble starches when reconstituted in water. The principal soluble constituent is glucomannan, a polysaccharide comprised of D-glucose and D-mannose, which is useful as an ingredient in various foodstuffs, as well as in industrial applications such as films, oil drilling fluids, and paints.

There are numerous impurities in crude, native, konjac flour, principally insoluble starches, cellulose, and nitrogen-containing materials, including proteins, many of which impurities are derived from "sacs" which encapsulate the konjac flour in the tuber.

Konjac glucomannan has been shown to readily degrade in the digestive tract. See Japanese patent application number 57185216 A2.

It would be beneficial to have a konjac glucomannan with enhanced properties to enable its use in sustained release applications.

SUMMARY OF THE INVENTION

This invention provides a solid dosage form having sustained release properties, preferably for non-food, most preferably for pharmaceutical, applications. The formulation includes a readily available konjac glucomannan which is exemplified by, but not limited to, a dry clarified konjac glucomannan, or a rapidly hydratable konjac glucomannan such as cryogenically ground konjac or plasticized konjac as a sustained release excipient. The readily available konjac glucomannan can be mixed with a dry active material, and a solid dosage form prepared.

DESCRIPTION OF THE PREFERRED EMBODIMENTS

Crude Konjac

The term "crude" konjac, as used herein, refers to an unclarified or native konjac flour in which the glucomannan is still contained in the sacs in which it occurs in nature, and various other impurities may be present. Further clarification of the terms clarified konjac and cryogenically ground konjac is provided in U.S. patent application Ser. No. 742,136 filed 8/8/91 which is hereby incorporated by reference.

Readily Available Konjac

Crude konjac glucomannan is not readily available to the system because it is isolated from the system by the sac walls of the konjac plant. Traditional grinding techniques do not completely break down those walls. As a consequence, traditionally prepared konjac glucomannan if used as an excipient would exhibit a less predictable timed release rate and it would hydrate too slowly to make it as effective a time release excipient.

Readily available konjac glucomannan is defined by the fact that it readily dissolves in deionized water at 25° C., whereas crude konjac will not dissolve readily without heating to more elevated temperatures. Readily available konjac glucomannan readily hydrates and when hydrated forms a high viscosity system. These properties provide significant sustained release properties for the solid dosage forms.

Some readily available konjac glucomannans include clarified konjac and rapidly hydratable konjac. Rapidly hydratable konjac is a generic term which includes as species cryogenically ground konjac and plasticized konjac.

Rapidly Hydratable Konjac

Rapidly hydratable konjac flour is characterized by a percentage potential viscosity gain of at least 60% after a 10 minute period, of at least 80% after a 20 minute period, and/or of from 80 to 100% after a 30 minute period, all measured in water at 25° C. and all based upon a predetermined 100% maximum viscosity gain. Rapidly hydratable konjac can be produced by cryogenic grinding or by the process of moistening native konjac flour to plasticize it, then milling it to form a flake, followed by grinding the flake. Both cryogenically ground konjac and plasticized konjac described below are forms of rapidly hydratable konjac. A further elaboration on these forms of konjac is found in U.S. patent application Ser. No. 770801 filed Oct. 03, 1991, entitled "Rapidly Hydratable Konjac" which is herein incorporated by reference.

Clarified Konjac

The term "clarified konjac" as used herein, denotes a konjac glucomannan flour that is capable of forming a clear sol. Additionally, clarified konjac is substantially free of insoluble impurities, and has a lower nitrogen content than unclarified konjac. A clear sol is defined to be an aqueous sol that has a turbidity of no greater than 100 turbidity units as measured at 1.0 w/v % concentration using the Formazin turbidity standard. Preferably, the clarified konjac will be characterized by a nitrogen content of 0.60 wt % or less and an aqueous sol turbidity potential from 20 to 70 turbidity units as measured at 1.0 w/v % concentration using the Formazin turbidity standard. More preferably the clarified konjac is characterized by a nitrogen content of 0.175 wt % or less and an aqueous sol turbidity potential of 20 to 70 turbidity units. Most preferably, the clarified konjac is characterized by a nitrogen content of 0.15 wt % or less and an aqueous sol turbidity potential of 20 to 60 turbidity units.

Properties of Clarified Konjac

Clarified konjac affords advantages over unclarified (crude) konjac flour, namely improved odor, color, solubility, hydratability, and grindability. Crude konjac has a known distinct odor, and a tan to dark brown color (as a dry powder). Furthermore, crude konjac particles are not uniform in size and cannot be ground at normal milling temperatures. Milling or other such grinding of crude konjac produces high temperatures which destroy its viscosity potential in much the same way as dry heat degradation, and which contribute to its dark color. By contrast, clarified konjac is a white powder which forms a clear sol, is odor-free and can readily be ground to a uniform size. Additionally, clarified konjac is more uniform in glucomannan content, and thus avoids the wide, uncontrolled variations in viscosity or gel strength which occur with crude konjac.

Another desirable property of clarified konjac powder is that, unlike crude konjac powder, clarified konjac hydrates in a manner more favorable to sustained release.

An important benefit of clarified konjac over crude konjac is that it is more stable as a dry powder. For example, crude konjac stored for 4 weeks at above room temperature (50° C.) loses 80% of its aqueous sol viscosity potential. By contrast, clarified konjac stored for the same time and at the same temperature loses only about 20% of its viscosity potential. It is believed that the increased storage stability is the result of the denaturing of enzymes present in the crude material, both by the initial heating of the sol and by the subsequent alcohol wash during the clarification process. It is a further benefit of clarification that clarified konjac is more easily rehydratable than crude konjac.

While the turbidity of flour and product samples is generally determined by using visible light, ultraviolet (UV) light may also be employed to characterize the clarified product and gauge the effectiveness of clarification procedures. This may be achieved by preparing 0.5% sols of product, placing them in cuvettes and measuring their UV absorbance between 200 and 320 nanometers (nm). Impurities, including DNA and protein, absorb UV light in the 260–280 nm region and peaks in this area indicate their presence and relative amounts. Crude konjac samples contain a broad peak in this region and, overall, have a higher baseline of absorbance than clarified konjac samples, which lack the 260–280 peak. This is especially important for a biotechnology separation medium where the presence of DNA or protein might interfere with performance.

Cryogenically Ground Konjac

Cryogenically ground konjac is konjac flour ground at a temperature which is sufficiently cooling-effective to prevent konjac flour degradation as evidenced by browning or by an undesirable smell.

Plasticized Konjac Flour

Plasticized konjac flour is a konjac flour produced by first moistening native konjac flour to plasticize it, and then milling it to form a flake followed by grinding the flake.

Pharmaceutical Preparations

The solid dosage forms may be used to deliver any pharmaceutically active component. The dosage forms may include analgesics, antibiotics, antiepileptics, antihistamines, cough and cold drugs, cardiovascular drugs, gastrointestinal drugs, respiratory drugs, and other drugs. A few illustrative examples are provided below. *Analgesics: acetominophen, ibuprofen, ketoprofen and the like, indomethacin, naproxen, acetaminophen with codeine and acetaminophen with propoxyphene napsylate. *Antibiotics: erythromycin, cephalosporins, minocyclin HCl. *Antiepileptics: phensuximide, phenytoin sodium and valproate sodium. * Antihistamines: chlorpheniramine maleate, diphenhydramine hydrochloride, triprolidine hydrochloride. *Cough and Cold drugs: dextromethorphan hydrobromide, ephedrine sulfate, guaifenesin, phenypropanolamine hydrochloride, promethazine hydrochloride, and pseudoephedrine hydrochloride. *Cardiovascular Drugs: captopril, chlorthiazide and hydrochlorthiazide, diltiazem, nadolol, papaverine hydrochloride, propranolol hydrochloride, quinidine gluconate, quinidine sulfate. *Gastrointestinal Drugs: cimetidine, loperamide hydrochloride and ranitidine. *Respiratory Drugs: albuterol sulfate, aminophylline, theophylline.

SOLID DOSAGE FORMS

Them are a variety of solid dosage forms which are available. A few illustrative examples include the following: tablets, beads, balls, spheres, cakes, compacts, granules, bars, briquettes and the like. The forms may be prepared by a number of methods including, but not limited to, the following: compression molding, extrusion, pelletization, slugging, roller compaction, granulation, die casting, briquette formation, or other solid dosage form preparation methods.

The solid dosage forms are usable in a wide variety of fields of use including agricultural and veterinary products, pharmaceuticals, swimming pool additives, industrial biocides, cosmetics, household pesticides, and dye manufacturing. Thus the active ingredients can be a pesticide, a herbicide, an active veterinary composition, a pharmaceutically active ingredient, a swimming pool additive, an industrial biocide or other active ingredient.

TABLETTING AIDS

Tabletting aids, commonly used in tablet formulating can be used. These include, but are not limited to lubricants, glidants, stabilizing agents, fillers, surfactants and the like. These can be selected and utilized by those skilled in the art according to the needs at hand without undue experimentation.

As an alternative to, or in addition to, the hydrocolloid gum as a sustained release excipient gum adjunct, a lactose filler may be utilized. Illustrative examples of fillers include the following: lactose, starch, sucrose, dicalcium phosphate, magnesium carbonate, microcrystalline cellulose, floc cellulose, and various saccharides and polysaccharides known to those skilled in the tabletting art.

PREPARATION

The method of preparing a pharmaceutical tablet is also contemplated as being within the scope of the invention. The tablet is formed by blending the excipient and the pharmaceutically active compound, and applying suitable pressure to effect tablet formation. For simple compaction of ½ inch tablets on a hydraulic press, pressures of at least 2000 psi are suitable. Generally, the crushing strength of the final tablet is preferred to be in the range of 6 to 12 kg. (as measured according to the method in example 1A).

One of the features of the readily available konjac glucomannan excipient described herein is that sustained release tablets can be compounded dry by direct compression, such as of dry powders. More particularly, these dry powders need not have been previously conditioned by prewetting or prehydrating. Techniques do exist where such conditioning is efficacious although more costly. Generally, such preconditioning with water (wet granulation) improves the ability of the excipient to serve its function as a binding agent for the solid dosage form permitting the use of a smaller weight percent of the excipient.

Generally, at least 4 wt % of the rapidly hydratable konjac sustained excipient will be utilized. Preferably from 7 to 50 wt % excipient will be used based on tablet weight. More preferably from 10 to 40 wt % of the excipient will be used and most preferably, from 10 to 30 wt % will be utilized.

Another embodiment of the invention includes a hydrocolloid gum used in conjunction with the sustained release excipient, as an adjunct gum. Xanthan gum exhibits both enhanced hydration and viscosity increase on a weight basis when used in conjunction with the clarified konjac, permitting the utilization of less clarified konjac in the tablet formulation and the inclusion of a greater weight percent of pharmaceutically active material in the tablet.

An effective ratio of sustained release excipient to adjunct gum can be selected without undue experimentation. There is no upper limit to the ratio. However, for synergistic effect a ratio within the range of 20:1 to 1:1 is preferred. More preferred is a ratio within the range of from 15:1 to 5:1, and most preferred is a ratio within the range of from 12:1 to 6:1.

EXAMPLES

Solid dosage forms and methods of preparing them are described in Example 1 through 8 below. A summary table is provided after the last example.

Example 1

Sustained Release Tablets Prepared Using Clarified Konjac Flour mixture 1A

A mixture of 4.9588 g of anhydrous theophylline which passed through a 40 mesh U.S. Standard screen (420 microns) and 2.1252 g of clarified konjac flour were thoroughly blended in a screw-top jar for a period of eight minutes. The konjac flour had been prepared by precipitation of the konjac from an aqueous solution by pouring it into isopropanol, drying the precipitate, and grinding the dried material. The ground material had been passed through a 60 mesh (250 microns) screen.

A 0.500 g portion of this mixture was placed in a 0.5 inch (1.270 cm) diameter stainless steel punch and die. The punch and die set was placed in a Carver press, and the pressure was increased to 4000 psi (27,580 KPa) and held there for 5 seconds. The resulting flat-faced tablet was 2.93 mm thick and had an average crushing strength of 10.6 kg. Crushing strength, sometimes referred to as hardness, was measured in a Schleuniger-4M Hardness Tester which applies pressure across the diameter of the tablet with horizontally opposed, flat anvils, the measurement being the force required to crush the tablet. The sustained release performance of the tablets was investigated by measuring their disintegration and dissolution properties. The disintegration of these tablets in aqueous media was measured in an apparatus defined in the U. S. Pharmacopeia (USP XX) in which tablets are placed in standardized wire mesh baskets which are moved vertically in an aqueous fluid kept at a constant 37° C. In some instances, after the tablet was placed in the basket, a perforated plastic disk of specified dimensions and design was also placed in the basket. These disks were used to determine the disintegration characteristics of the tablets prepared in this experiment, providing the following results: In a pH=1 aqueous solution the tablets developed a protective gel within one hour, maintain their integrity for more than six hours; the tablets, however, had completely disintegrated by the seventh hour. In deionized water (pH=7) a thick gel formed and persisted for an entire seven hour period at the end of which time the tablet was still visible. At pH=7.4 the behavior was more nearly the same as that at pH=1, although traces of the disk remained after seven hours. Dissolution of the tablets in 900 mL of deionized water was then measured using USP Apparatus 2 with the rotating paddle being operated at 50 rpm. The following table shows the cumulative amount of theophylline in solution as measured by a Beckman DU-7 uv/visible spectrophotometer at 272 nm at hourly intervals:

| Elapsed Time (hours) | Cumulative Percentage Theophylline in Solution |
| --- | --- |
| 1 | 58 |
| 2 | 65 |
| 3 | 67 |
| 4 | 70 |
| 5 | 72 |
| 6 | 74 |

Note:
A tablet allowed to rest in the deionized water without agitation for one minute exhibited significantly reduced release of theophylline during the first hour (42%), but similar incremental releases during subsequent hours.

Mixture 1B

A second set of 0.500 g tablets was prepared from a mixture of 1.1550 g of theophylline and 0.4950 g of the clarified konjac flour which had been further treated by removal of all konjac flour particles which did not pass through a 140 mesh (105 microns) screen. As before, these tablets were prepared at 4000 psi (27,580 KPa) for five seconds. The tablets were 2.93 mm thick and exhibited a crushing strength of 10.6 kg. The dissolution testing of these tablets in deionized water provided the following results:

| Elapsed time (hours) | Cumulative Percentage Theophylline in Solution |
| --- | --- |
| 1 | 38 |
| 2 | 47 |
| 3 | 51 |
| 4 | 54 |
| 5 | 57 |
| 6 | 60 |

EXAMPLE 2

Sustained Release Tablets Prepared Using Combinations of Clarified Konjac Flour and Xanthan Gum Mixture 2A A dry mixture of 2.4500 g of theophylline, 0.7003 g of clarified konjac flour (having a particle of <105 microns in diameter), and 0.3500 g of xanthan gum was prepared and blended well for five minutes.

Tablets weighing 0.500 g were prepared by the method of Example 1 at a pressure of 3400 psi (23,440 KPa). The resulting tablets were 2.94 mm thick and had a crushing strength of 10.3 kg. The disintegration test was performed in the manner of Example 1 in deionized water except that the perforated disk was placed in the basket five minutes after the test had begun. A rough gel formed on the tablet within five minutes, but the tablet completely dissolved within 2.5 hours.

Mixture 2B

To 1.500g Mixture 2A were added an additional 1.053 g of theophylline and 0.457 g of the clarified konjac flour. This reduced the ratio of theophylline:konjac flour:xanthan gum from 7:2:1 to 14:5:1.

Tablets were prepared from this mixture by the method of Example 1 at a pressure of 3800 psi (26,200 KPa). These tablets had a crushing strength of 10.2 kg. Disintegration tests on these tablets yielded the following results in deionized water: Without using the perforated disk, the tablet formed a rough gel within five minutes and after four hours there was still a coherent gel present with some white particles visible. Another tablet was placed in the basket without the perforated disk for five minutes after which the disk was placed in the basket; this tablet initially behaved similarly to the first one tested, but it was not visible after four hours.

Mixture 2C

For comparative purposes, a mixture of 4.550 g theophylline and 1.950 g clarified konjac flour was prepared and blended thoroughly for five minutes.

Tablets weighing 0.500 g were prepared from this mixture at a pressure of 3000 psi (20,680 KPa). These tablets were 3.02 mm thick and had a crushing strength of 10.1 kg. Disintegration testing was performed on these tablets, yielding the following results: In a pH=1 solution the gel required nearly one hour to form and the tablets then survived for nearly seven hours, disappearing at the end of this period. In deionized water a gel formed within two minutes and the tablet had completely disappeared at the end of 1.5 hours. At pH=7.4 a thin gel formed within 15 minutes, but the tablet was completely gone at the end of 2.5 hours.

Example 3

Sustained Release Tablets Prepared Using Non-clarified Cryogenically Ground Konjac Flour

Mixture 3A

A mixture of 7.230 g of theophylline and 3.099 g of crude konjac flour which had been ground under cryogenic conditions was thoroughly blended for five minutes by the method of Example 1. The cryogenically ground konjac had the following particle size distribution on a weight percent basis:

| | |
|---|---|
| >60 mesh (>250 microns) | 0.4% |
| >100 mesh (150–250 microns | 4.0% |
| >140 mesh (105–150 microns) | 11.0% |
| >200 mesh (75–105 microns) | 24.0% |

-continued

| | |
|---|---|
| <200 mesh (<75 microns) | 60.6% |

Tablets of this mixture weighing 0.500 g were prepared by the method of Example 1 at a pressure of 4400 psi (30,340 KPa) for 5 seconds. The resulting tablets were 2.85 mm thick and had a crushing strength of 10.4 kg. The disintegration test was performed at pH=1, pH=7 (deionized water), and pH=7.4. In all media the tablets survived in good shape for six hours. The greatest initial changes in the shape of the tablets occurred at pH=1. Dissolution testing in deionized water yielded the following results:

| Elapsed Time (hours) | Cumulative Percentage Theophylline in Solution |
|---|---|
| 1 | 16 |
| 2 | 21 |
| 3 | 24 |
| 4 | 28 |
| 5 | 31 |
| 6 | 34 |

Mixture 3B

A second mixture composed of 80% by weight theophylline and 20% by weight of cryogenically ground konjac flour was blended thoroughly. Tablets weighing 0.500 g were prepared in the manner of Example 1 at a pressure of 4500 psi (31,030 KPa) for five seconds. These tablets had a crushing strength of 10.9 kg. Dissolution testing in deionized water yielded the following results:

| Elapsed Time (hours) | Cumulative Percentage Theophylline in Solution |
|---|---|
| 1 | 20 |
| 2 | 25 |
| 3 | 29 |
| 4 | 33 |
| 5 | 36 |
| 6 | 39 |

Example 4

Sustained Release Tablets Prepared Using Non-clarified Cryogenically Ground Konjac Flour and Xanthan Gum

Mixture 4A

A mixture of 6.00 g of theophylline, 2.31 g of cryogenically ground konjac flour (Example 3), and 0.257 g of Keitrol F xanthan gum was blended thoroughly. Tablets weighing 0.500 g were prepared in the manner of Example 1 at 5000 psi (34,470 KPa). These tablets had a crushing strength of 9.9 kg. Dissolution testing of these tablets in deionized water yielded the following results:

| Elapsed Time (hours) | Cumulative Percentage Theophylline in Solution |
| --- | --- |
| 1 | 6 |
| 2 | 9 |
| 3 | 11 |
| 4 | 13 |
| 5 | 15 |
| 6 | 17 |

Mixture 4B

A second mixture of 6.40 g of theophylline, 1.440 g of non-clarified cryogenically ground konjac flour, and 0.160 g of xanthan gum was blended thoroughly for eight minutes. Tablets weighing 0.500 g were made from this mixture by the method of Example 1 at a pressure of 4300 psi (29,650 KPa) for five seconds. These tablets were 2.85 mm thick and had a crushing strength of 10.7 kg. Dissolution testing of these tablets in deionized water yielded the following results:

| Elapsed Time (hours) | Cumulative Percentage Theophylline in Solution |
| --- | --- |
| 1 | 5 |
| 2 | 8 |
| 3 | 10 |
| 4 | 12 |
| 5 | 14 |
| 6 | 15 |

Mixture 4C

A third mixture of 6.40 g of theophylline, 1.400 g of cryogenically ground konjac flour, and 0.200 g of Keltrol F xanthan gum was thoroughly blended. Tablets weighing 0.500 g were prepared by the method of Example 1 at a pressure of 4300 psi (29,650 KPa) for five seconds. These tablets were 2.86 mm thick and had a crushing strength of 10.7 kg. Dissolution testing of these tablets in deionized water yielded the following results:

| Elapsed Time (hours) | Cumulative Percentage Theophylline in Solution |
| --- | --- |
| 1 | 5 |
| 2 | 7 |
| 3 | 9 |
| 4 | 11 |
| 5 | 13 |
| 6 | 14 |

Example 5

Sustained Release Tablets Prepared Using Cryogenically Ground Konjac Flour and Lactose A mixture containing 80% by weight theophylline, 10% by weight cryogenically ground konjac flour, and 10% by weight lactose (Fast-flo® 316 lactose nutrient, Fast-flo is a trademark of Foremost for a lactose product) was blended thoroughly. Tablets weighing 0.500 g were prepared by the method of Example 1 at a pressure of 4300 psi (29,650 KPa) for five seconds; and they exhibited a crushing strength of 12.1 kg. Dissolution testing of these tablets in deionized water yielded the following results:

| Elapsed Time (hours) | Cumulative Percentage Theophylline in Solution |
| --- | --- |
| 1 | 47 |
| 2 | 55 |
| 3 | 61 |
| 4 | 66 |
| 5 | 69 |
| 6 | 73 |

Example 6

Sustained Release Tablets Prepared Using Cryogenically Ground Konjac Flour, Xanthan Gum, and Lactose Mixture 6A A mixture of 6.40 g of theophylline, 0.720 g of cryogenically ground konjac flour, 0.080 g of Keltrol F xanthan gum, and 0.800 g of lactose (Fast-flo 316) was blended thoroughly for four minutes. Tablets weighing 0.500 g were made from this mixture by the method of Example 1 at a pressure of 4500 psi (31,030 KPa) for five seconds. These tablets were 2.84 mm thick and had a crushing strength of 11.9 kg. Dissolution testing of these tablets in deionized water yielded the following results:

| Elapsed Time (hours) | Cumulative Percentage Theophylline in Solution |
| --- | --- |
| 1 | 6 |
| 2 | 9 |
| 3 | 12 |
| 4 | 14 |
| 5 | 16 |
| 6 | 18 |

Mixture 6B

A second mixture of 8.000 g of theophylline, 0.450 g of cryogenically ground konjac flour, 0.050 g of Keltrol F xanthan gum, and 1.500 g of lactose (Fast-flo 316) was thoroughly blended. Tablets of this mixture, weighing 0.500 g, were prepared by the method of Example 1 at a pressure of 4600 psi (31,720 KPa) for five seconds. These tablets were 2.86 mm thick and had a crushing strength of 11.0 kg. Dissolution testing of these tablets in deionized water yielded the following results:

| Elapsed Time (hours) | Cumulative Percentage Theophylline in Solution |
| --- | --- |
| 1 | 13 |
| 2 | 18 |
| 3 | 23 |
| 4 | 27 |

| Elapsed Time (hours) | Cumulative Percentage Theophylline in Solution |
| --- | --- |
| 5 | 32 |
| 6 | 36 |

Example 7

Sustained Release Tablets Prepared Using Nutricol®K80V Konjac Flour

A mixture of 7.00 g of theophylline and 3.00 g of Nutricol®Konjac* K80V flour were thoroughly blended for five minutes by the method of Example 1. Nutricol®K80V konjac is a trademark of FMC Corporation for a crude konjac flour having 9.0/weight percent dextrose. The Nutricol® Konjac K80V had the following particle size distribution:

| | |
| --- | --- |
| >420 microns | 3.78% |
| 250–420 microns | 50.54% |
| 150–250 microns | 27.34% |
| 105–150 microns | 7.96% |
| 74–105 microns | 2.28% |
| <74 microns | 8.10% |

*Nutricol is a trademark of FMC Corporation for a crude konjac flour.

Tablets of this mixture weighing 0.500 g were prepared by the method of Example 1 at a pressure of 9000 psi (62,070 KPa) for 5 seconds. The resulting tablets were 3.76 mm thick and had a crushing strength of 10.9 kg. The disintegration test was performed in deionized water. The tablet fell apart easily within 2 minutes without using a perforated disk.

Example 8

Sustained Release Tablets Prepared Using USP Grade Hydroxypropyl Methylcellulose Mixture 8A A mixture of 700 g of theophylline and 300 g of hydroxypropyl methylcellulose (Methocel®K4M USP, The Dow Chemical Company, Midland, Mich.) was blended in a polyethylene bag by shaking and tumbling motions for a period of ten minutes. Tablets of this mixture weighing 0.500 g were prepared by the method of Example 1 at a pressure of 2600 psi (17,930 KPa) for five seconds. These tablets were 3.17 mm thick and had a crushing strength of 10.2 kg as measured 24 hours after being prepared. Results of disintegration testing in the presence of a perforated disk in three aqueous media are: In pH=1 after 30 minutes a lumpy gel had formed over the entire surface, at one hour the tablet was adhering to the perforated disk, and at five hours the tablet was greatly reduced in size, disappearing completely after 5.5 hours. In deionized water similar observations were made except that there was a small tablet remaining after 5.5 hours. At pH=7.4 similar observations were made except that the tablet was still intact at 5.5 hours and was stuck to the bottom of the mesh basket in which it was being tested. Dissolution testing of these tablets in deionized water yielded the following results:

| Elapsed Time (hours) | Cumulative Percentage Theophylline in Solution |
| --- | --- |
| 1 | 8 |
| 2 | 12 |
| 3 | 15 |
| 4 | 18 |
| 5 | 21 |
| 6 | 24 |

Mixture 8 B

A second mixture of 80.0 g of theophylline and 20.0 g of hydroxypropyl methylcellulose (Methocel K4M USP) was mixed in a polyethylene bag for ten minutes. Tablets of this mixture weighing 0.500 g were prepared by the method of Example 1 at a pressure of 2600 psi (17,930 KPa) for five seconds. These tablets were 3.16 mm thick and had a crushing strength of 8.7 kg as measured 24 hours after the tablets were made. Disintegration testing in the aqueous media provided the following results: In pH=1 a gel began to appear after 15 minutes, and at 60 minutes the tablet was covered by a rough gel. After three hours the tablet was significantly smaller, and at 5.5 hours a perforated disk was added to the basket to prevent the tablet from floating out of the basket. At 7 hours the tablet was still intact, but it consisted primarily of gel with a small, soft, dry center. Similar observations were made in deionized water and at pH=7.4 except that these tablets were still intact at 7 hours and had less gel associated with the dry center. Dissolution testing of these tablets in deionized water yielded the following results:

| Elapsed Time (hours) | Cumulative Percentage Theophylline in Solution |
| --- | --- |
| 1 | 8 |
| 2 | 12 |
| 3 | 15 |
| 4 | 18 |
| 5 | 21 |
| 6 | 24 |

Summary Table
The following table provides a summary of the examples above.

| Example No. | Total Weight Theophylline | Konjac Weight % | Xanthan | Lactose | (PSI) Compress Pressure | Crushing Strength (kg) |
|---|---|---|---|---|---|---|
| 1A | 70 | 30 (<250 microns, μm) | | — | 4000 | 10.6 |
| B | 70 | 30 (<105 microns, μm) | | — | 4000 | 10.6 |
| 2A | 70 | 20 | 10 | — | 3400 | 10.3 |
| B | | | | | | |
| C | 70 | 25 | 5 | — | 3800 | 10.2 |
| 3A | 70 | 30 | — | — | 4400 | 10.4 |
| B | 80 | 20 | — | — | 4500 | 10.9 |
| 4A | 70 | 27 | 3 | — | 5000 | 9.9 |
| B | 80 | 18 | 2 | — | 4100 | 10.7 |
| C | 80 | 17.5 | 2.5 | — | 4300 | 10.7 |
| 5 | 80 | 10 | — | 10 | 4300 | 12.1 |
| 6A | 80 | 9 | 1 | 10 | 4500 | 11.9 |
| B | 80 | 4.5 | 0.5 | 15 | 4600 | 11.0 |
| 7 | 70 | 27.3 | — | 2.7% dextrose | 9000 | 10.9 |
| 8 | hydroxypropyl methylcellulose | | | | | |
| A | 70 | 30 | — | — | 2600 | 10.2 |
| B | 80 | 20 | — | — | 2600 | 8.7 |

The tablets made according to this invention can have a variety of sustained release times depending on the pharmaceutically active drug with which the sustained release excipient is used, the relative amount of adjunct gum, the relative amount of fillers such as lactose, and the presence of other tablet formulating ingredients such as lubricants and binders.

Sustained release times can be adjusted by varying the ingredients and their proportions. In pharmaceutical uses release times can be shortened to allow complete release in the stomach or lengthened to also permit release in the intestinal tract. Thus the sustained release excipients permit the preparation of tablets which exhibit a sustained release at a pH $\geq 1$. Preferred is a pH range of 1 to 7.4. In practice, release times for Other applications can similarly be predetermined using tablet test conditions simulating the environment the dosage form will be subjected to.

We claim:

1. A solid dosage form, comprising an active ingredient and a sustained release excipient which excipient is at least 7 weight percent of a readily available konjac glucomannan based on the weight of the solid dosage form, wherein the dosage form contains no gas producing disintegrant.

2. The solid dosage form of claim 1, wherein:
   the amount of readily available konjac glucomannan sustained release agent is 7 to 50 wt%, and
   the readily available konjac glucomannan and the active were compounded dry without having been previously conditioned by wetting of hydrating.

3. The solid dosage form of claim 2, further including xanthan gum, wherein the weight ratio of readily available konjac glucomannan to xanthan gum is within the range of from 15:1 to 5:1 and the sustained release time within the range of 3 to 12 hours at a pH within the range of 1 to 7.4.

4. The solid dosage form of claim 2, further including xanthan gum, wherein the weight ratio or readily available konjac glucomannan to xanthan gum is within the range of 12:1 to 6:1.

5. The solid dosage form of claim 1, wherein:
   the amount of readily available konjac glucomannan sustained release agent is 10 to 40 wt%; and
   the readily available konjac glucomannan and the active were compounded dry without having been previously conditioned by wetting or hydrating.

6. The solid dosage form of claim 5, further including xanthan gum, and wherein the weight ratio of readily available konjac glucomannan to xanthan gum is within the range of 20:1 to 1:1 and exhibits a sustained time release at a pH of approximately I to 7.4.

7. The solid dosage form of claim 5 further including xanthan gum, wherein:
   the readily available konjac is a rapidly hydratable konjac
   the ratio of rapidly hydratable konjac sustained release excipient to xanthan gum is within the range of from 12:1 to 6:1, and
   the sustained release time is within the range of from 3 to 10 hours.

8. The solid dosage form of claim 5, wherein the readily available konjac is selected from the group consisting of clarified konjac, cryogenically ground konjac, and plasticized konjac.

9. The solid dosage form of claim 1, further including xanthan gum, and
   wherein:
   the weight ratio of readily available konjac glucomannan to xanthan gum is within the range of 20:1 to 1:1; and
   the readily available konjac glucomannan, xanthan gum and the active were compounded dry without having been previously conditioned by wetting or hydrating.

10. The solid dosage form of claim 9, wherein the readily available konjac glucomannan is selected from the group consisting of clarified konjac, cryogenically ground konjac, and plasticized konjac.

11. The solid dosage form of claim 9, wherein the solid dosage form has a sustained release time within the range 3 to 12 hours at a pH within the range of 1 to 7.4.

12. The solid dosage form of claim 1, wherein the readily available konjac glucomannan is selected from the group consisting of clarified konjac, cryogenically ground konjac, and plasticized konjac.

13. Solid dosage forms as in any of claims 1 to 8 in the form of a tablet.

14. Solid dosage forms as in any of claims 1 to 8, wherein the active ingredient is a pharmaceutically active ingredient and wherein the solid dosage form is a tablet.

15. A method for making a pharmaceutical tablet comprising the steps of forming a mixture of a dry pharmaceutically active ingredient with a sustained release excipient of at least 7 weight percent of a dry, readily available konjac glucomannan, and compressing the dry mixture at a pressure sufficient to form a table with a hardness of at least 6 kg, wherein no gas producing disintegrant is included in the tablet.

16. The method of claim 15, wherein the readily available konjac glucomannan excipient is within the range of from 7 to 50 wt %.

17. The method of claim 16, wherein compressing the dry mixture is by direct compression which occurs at a pressure sufficient to form a tablet with a hardness within the range of 8 to 14.

18. The method of claim 17, further including admixing xanthan gum with the readily available konjac glucomannan in a ratio within the range of 20:1 to 1:20 prior to the direct compression step.

19. The method of claim 18, wherein the ratio of readily available konjac glucomannan to xanthan gum is within the range of 6:1 to 12:1.

20. The pharmaceutical formulation of claim 19, wherein the readily available konjac glucomannan is selected from the group consisting of clarified konjac, cryogenically ground konjac, and plasticized konjac.

21. The pharmaceutical formulation of claim 17, wherein the readily available konjac glucomannan is selected from the group consisting of clarified konjac, cryogenically ground konjac, and plasticized konjac.

22. A sustained release excipient consisting essentially of readily available konjac glucomannan.

23. A solid dosage form, comprising an active ingredient and a sustained release excipient which excipient consists essentially of at least 7 weight percent of a readily available konjac glucomannan based on the weight of the solid dosage form, wherein the dosage form contains no gas producing disintegrant.

24. A method for making a pharmaceutical tablet comprising the steps of forming a mixture of a dry pharmaceutically active ingredient with a sustained release excipient consisting essentially of at least 7 weight percent of a dry, readily available konjac glucomannan, and compressing the dry mixture at a pressure sufficient to form a table with a hardness of at least 6 kg, wherein no gas producing disintegrant is included in the tablet.

* * * * *